(12) United States Patent
Lesic

(10) Patent No.: US 10,821,481 B1
(45) Date of Patent: Nov. 3, 2020

(54) DISINFECTING WIPE

(71) Applicant: Zoran Lesic, Denver, CO (US)

(72) Inventor: Zoran Lesic, Denver, CO (US)

(*) Notice: Subject to any disclaimer, the term of this patent is extended or adjusted under 35 U.S.C. 154(b) by 280 days.

(21) Appl. No.: 16/120,649

(22) Filed: Sep. 4, 2018

Related U.S. Application Data

(60) Provisional application No. 62/554,079, filed on Sep. 5, 2017.

(51) Int. Cl.
| | |
|---|---|
| A47L 13/12 | (2006.01) |
| A47L 13/25 | (2006.01) |
| A47L 13/256 | (2006.01) |
| B08B 1/00 | (2006.01) |
| B08B 3/08 | (2006.01) |
| B32B 5/02 | (2006.01) |
| B32B 3/28 | (2006.01) |
| A61L 2/26 | (2006.01) |
| A61L 2/18 | (2006.01) |
| B32B 7/05 | (2019.01) |

(52) U.S. Cl.
CPC .............. *B08B 1/006* (2013.01); *A47L 13/12* (2013.01); *A47L 13/256* (2013.01); *A61L 2/18* (2013.01); *A61L 2/26* (2013.01); *B08B 3/08* (2013.01); *B32B 3/28* (2013.01); *B32B 5/022* (2013.01); *B32B 7/05* (2019.01); *A61L 2202/17* (2013.01); *B32B 2432/00* (2013.01)

(58) Field of Classification Search
CPC .......... A47L 13/12; A47L 13/25; A47L 13/16; B08B 1/006; A61L 2/18
See application file for complete search history.

(56) References Cited

U.S. PATENT DOCUMENTS

| | | | |
|---|---|---|---|
| 2,960,561 A | 11/1960 | Plummer | |
| 4,145,001 A * | 3/1979 | Weyenberg | A61L 9/12 239/56 |
| 4,939,819 A | 7/1990 | Moyer | |
| 5,127,127 A | 7/1992 | Jarosinski | |
| 5,127,423 A | 7/1992 | Draeger | |
| 5,187,813 A | 2/1993 | Klein | |
| 5,788,155 A * | 8/1998 | Martin | A61L 9/12 239/34 |
| 5,918,341 A * | 7/1999 | Hale | B24D 15/04 15/104.93 |
| 5,964,351 A | 10/1999 | Zander | |
| 6,010,001 A | 1/2000 | Osborn, III | |
| 6,030,331 A | 2/2000 | Zander | |
| 6,108,855 A * | 8/2000 | DeLeon | A01K 97/00 15/208 |
| 6,115,872 A * | 9/2000 | Welsh | A63B 57/60 15/209.1 |
| 6,142,297 A | 11/2000 | Price | |

(Continued)

*Primary Examiner* — Michael D Jennings
(74) *Attorney, Agent, or Firm* — FisherBroyles LLP; Ian R. Walsworth

(57) ABSTRACT

A wipe system is provided that is comprised of an inner portion sealed within an outer portion before use. The inner portion, which is used for cleaning, for example, may be wetted or saturated with a disinfecting fluid. Removal of an edge associated with the outer portion allows it to be opened to expose the inner portion. The wipe remains interconnected to the outer portion during use so that an opposite side of the outer portion is the only surface in contact with the user's hand.

17 Claims, 6 Drawing Sheets

(56) References Cited

U.S. PATENT DOCUMENTS

| | | | |
|---|---|---|---|
| 7,219,388 B2 * | 5/2007 | Hale | A47K 7/02 |
| | | | 15/209.1 |
| 8,066,118 B1 | 11/2011 | Van Tassell | |
| 8,795,438 B2 | 8/2014 | Rubin et al. | |
| 8,800,094 B1 * | 8/2014 | Robinson | C11D 17/049 |
| | | | 15/209.1 |
| 9,039,967 B2 | 5/2015 | Tennican et al. | |
| 9,125,600 B2 | 9/2015 | Steube | |
| 2007/0045135 A1 * | 3/2007 | Berger Sharp | A61K 8/0208 |
| | | | 206/229 |
| 2007/0048063 A1 * | 3/2007 | Bauer | B32B 27/32 |
| | | | 401/7 |
| 2007/0128411 A1 * | 6/2007 | Kawai | B32B 5/08 |
| | | | 428/170 |
| 2014/0020710 A1 * | 1/2014 | Williams | A47L 13/16 |
| | | | 134/6 |
| 2017/0050221 A1 * | 2/2017 | Naskrent | B32B 5/024 |

\* cited by examiner

DISINFECTING WIPE

This application claims the benefit of U.S. Provisional Patent Application Ser. No. 62/554,079, filed Sep. 5, 2017, the entirety of which is incorporated by reference herein.

FIELD OF THE INVENTION

Embodiments of the present invention are generally related to disinfecting wipes commonly used in a hospital setting.

BACKGROUND OF THE INVENTION

According to the CDC 1 in 20 hospitalized patients will contract a hospital-associated infection (HAI)—a major hazard and a threat to their safety. HAIs are often a cause of morbidity and mortality and they impose significant economic consequences on the nation's healthcare system.

While many pathogens can be transmitted by hand contamination, there are mechanisms in place to address this issue, such as hospital-wide incentives that remind health care workers to wash hands before and after seeing each patient. Conveniently available hand sanitizers are also often provided to help to minimize pathogen transmissions.

Patients may also be exposed to pathogens in contamination from tubing, trays, blood pressure cuffs, stethoscopes, etc. For example, transmission of infections through contaminated medical devices, such as stethoscopes. Indeed, stethoscopes are known to harbor various organisms on their diaphragm surfaces, including coagulase negative staphylococci, *Staphylococcus aureus, Corynebacterium* spp., *Bacillus* spp., *Neisseria* spp., alpha-hemolytic streptococci, *Micrococcus luteus, Enterococcus* spp., *Candida* spp., Gram negative organisms (including Pseudomonas aureginosa; also non-fermenting gram negative bacilli, including *Acinetobacteri* spp and *Stenotrophomanas maltophilia*), *Enterococcus faecalis, Escherichia coli, Aspergillus* spp., *Clostridium difficile*, common viruses (e.g. enteroviruses and small round structured viruses), and norovirus. Other objects in the healthcare setting can likewise be contaminated.

HAIs often begin with patient exposure to pathogenic bacteria that have colonized hospital equipment or personnel. Subsequent patient contact often leads to pathogen spread to the patients' skin, gut, or other systems which cause infection as the patient's normal body defenses are impaired through underlying diseases, administration of immunomodulating therapy, or use of invasive devices. The costs of hospital-associated infections are high. The annual cost to U.S. hospitals in 2007 ranged from $28.4 billion to $33.8 billion. According to the 2007 data, the attributable per patient costs of all HAIs ranged $16,359 to $19,430. Recent analyses indicate that at least 50% of HAIs are preventable, which could translate into significant savings for healthcare systems.

Studies support the need for clear disinfecting guidelines, outlining the need to disinfect devices, such as stethoscopes, before and after every patient contact to limit the bacterial load to which patients are exposed. However, currently available methods that employ disinfecting wipes are cumbersome, time-consuming, and inconvenient. Further, disinfecting wipes are often not available in a patient's room. These factors likely account for low compliance rates as convenience and availability appear to determine the method of stethoscope disinfection used by health care professionals.

The most popular disinfecting wipes used in the healthcare setting (CaviWipes™, SaniCloth®, Kimwipes™, etc.) are saturated in very effective disinfecting solutions, such as tertiary and quaternary amines; however, these solutions are harmful to skin and therefore the standard of care in the health care facilities is to use protective gloves when handling the wipes. One of ordinary skill in the art will appreciate that it is cumbersome to don and remove protective gloves multiple times per day and, thus, frequently routine disinfection practices are ignored. Furthermore, cost is an issue as each standard wipe requires two gloves and each standard box of gloves contains 100 gloves. Therefore, a pack of 100 wipes would require one to also use up two boxes of gloves; a pack of 150 wipes would require three boxes of gloves, etc. Therefore, the cost adds up fast as the "actual" cost of using standard wipes us also include the cost of gloves.

SUMMARY OF THE INVENTION

To address the issues outlined above, one embodiment of the present invention is a disinfecting wipe made up of an inner permeable layer containing the disinfecting agent(s) and the outer impermeable layer that protects the user's hands from the harmful disinfecting agent(s). Accordingly, the outer protective layer serves the function of protective gloves, thereby saving costs and encouraging healthcare professionals to comply with standard disinfecting protocols. An additional layer or layers may be positioned between the inner permeable layer and the outer impermeable layer to provide additional features and advantages. This layer(s) may possess as adhesive properties, accommodate disinfecting agent(s), absorb pathogens or inorganic/inanimate particles targeted by the user, etc.

The wipes of one embodiment are folded upon themselves and an airtight seal is provided around the edges. The inner permeable layer is contained in the airtight enclosure formed by the folded, outer impermeable layer. In this embodiment, at least a portion of the impermeable outer layer includes a selectively interconnectable border that creates the airtight seal that maintains the moisture content of the permeable inner layer. For example, a Ziploc® type closure device may be employed. In operation, the seal is broken, for example by pulling apart portions of the outer impermeable layer, and the inner permeable layer is exposed. The user applies the inner permeable layer onto a desired surface to disinfect the same while holding the outer layer. Accordingly, the user's fingers or hands never contact the disinfecting agent(s) or the targeted pathogens. A further advantage of this embodiment of the present invention is that separate packaging for the wipe is not needed as the outer impermeable layer functions as adequate packaging. However, some embodiments of the present invention employ additional packaging surrounding the exterior surface of the wipe to maintain sterility.

The fluid permeable material of the inner layer of one embodiment is made of nonwoven polypropylene. The inner layer is thermally bonded to the inner surface of the outer layer. Those of ordinary skill in the art will appreciate that adhesive may also be used to interconnect the inner layer to the outer layer without departing from the scope of the invention. Further, one embodiment of the present invention can be used multiple times. In this example, the outer layer includes an outer edge seal that is destroyed when first opened. An inner, selectively openable seal is spaced from the outer seal. Thus, the outer layer can be resealed and remaining moisture in the inner layer can be preserved after use. In addition, the inner layer may be capable of being re-wetted. In still other embodiments of the present invention, the inner layer may be selectively removed from the outer layer such that it can be replaced or cleaned and reused. In this embodiment, the inner layer is interconnected to the outer layer by way of a hook and loop fastening mechanism that allows for the inner layer to be maintained on the outer layer during use, but removal of the inner layer thereafter. As one of ordinary skill in the art will appreciate, all or portions of the outer layer and inner layer may be biodegradable or recyclable.

In another embodiment, a disinfecting solution is stored in an interior volume. The volume may comprise a pouch that is ruptured by pressing on or striking the wipe's outer layer. This embodiment of the present invention has the advantage of simplifying the manufacturing process as the sometimes-harmful disinfecting chemicals are contained during assembly. This aspect of some embodiments of the present invention is desirable because some disinfecting solutions could cause breakdown of common sealing or absorbent materials after time.

Besides being used for disinfection, the wipe system contemplated by this disclosure could be used for many other purposes that would require user's hands to be protected from noxious agents while applying them to the desired surface. That is, the disinfecting wipes of some embodiments of the present invention are not strictly limited to use in medical applications. One of ordinary skill in the art will appreciate that the wipes described herein can be used for household cleaning, automotive cleaning, wound care, as baby wipes, as polish applicators, etc. When used as baby wipes, the permeable inner layer may include flavor or a pleasing aroma so that children will not vehemently reject to their use.

Embodiments of the present invention enjoy additional benefits over wipes of the prior art, primarily avoiding the need for gloves because the outer layer is used to protect the user's hands. Further, the disinfecting wipes as described herein are easy-to-use, so healthcare providers will be more apt to follow standard disinfecting protocol. This aspect of embodiments of the present invention improves rates of disinfection compliance, which will result in a reduction of hospital-acquired infections and lower hospital operations cost and healthcare provider liability. In addition, some embodiments of the present invention include a stiffening layer that prevents the wipe from folding upon itself during use, which increases available surface area of the wipe and reduces the number of wipes needed to disinfect an object.

It is another aspect of some embodiments of the present invention to provide a wipe that signals loss of disinfecting solution efficacy. For example, the inner layer of one embodiment changes color when the disinfecting solution loses a predetermined degree of efficacy, dries beyond a predetermined degree, after predetermined amount of time, or after exposure to air or pathogens. Further, for wipes that employ a selectively-rupturable disinfecting solution pocket, the inner layer may change color when the pocket is broken to signal to the user that the disinfecting solution has been released. This functionality also allows the user to assess whether the wipe is working correctly or has already been used.

The wipe of one embodiment of the present invention is preferably formed from a ribbon of impermeable material with an absorbent material bonded on one side thereof. The assembly is cut to length to form an individual wipe. The material is then folded across the width of the wipe to form a volume that accommodates the inner layer. Depending on the shape of the volume, between one and three edges are made liquid-tight with a seal. This seal could be adhesive, thermally or sonically welded, or formed in some other manner.

In one embodiment, a pocket is added to the outer surface. The pocket is configured to receive at least one of the user's fingers to make cleaning easier (see, for example, U.S. Pat. No. 5,127,127).

It is an aspect of some embodiments of the present invention to provide a wipe, comprising: a rectangular first layer comprised of a substantially fluid impermeable material, the first layer having an outer boundary defined by an upper edge, a lower edge, a left lateral edge, and a right lateral edge, the first layer having a first, closed position of use, wherein the upper edge and lower edge are aligned, the left lateral edge is folded on itself, and the right lateral edge is folded on itself, and a second, open position of use, wherein the upper edge and lower edge are separated; a second layer at least partially comprised of a fluid permeable material interconnected to an inner surface of the first layer, the second layer having an outer boundary spaced from the outer boundary of the first layer, wherein when the first layer is in the first, closed position of use, portions of the first layer adjacent to the upper edge and the lower edge engage to form a first overlap area, portions of the left lateral edge engage to form a second overlap area, and portions of the right lateral edge form a third overlap area; a first bond provided on the first overlap area; a second bond provided on the second overlap area; a third bond provided on the third overlap area; and wherein the first bond, the second bond, and third bond form a substantially air-tight seal that is adapted to be selectively severed to allow removal of portions of the first layer adjacent to the outer boundary thereof to expose the second layer.

It is still yet another aspect of some embodiments of the present invention to provide a wipe, comprising: a fluid impermeable first layer having an outer edge, the first layer capable of being configured into a first, closed position of use, wherein the outer edge is divided to define a first outer edge portion that is aligned with a second outer edge portion, and a second, open position of use, wherein the first outer edge portion and second outer edge portion are separated; a second layer at least partially made of a fluid permeable material interconnected to an inner surface of the first layer, the second layer having an outer edge spaced from the outer edge of the first layer, wherein when the first layer is in the first, closed position of use, portions of the first layer adjacent to the outer edge thereof engage to form an overlap area that bounds the second layer; and a bond provided on the overlap area that forms a substantially air-tight seal that is adapted to be selectively severed to allow removal of portions of the first layer to expose the second layer.

The Summary of the Invention is neither intended nor should it be construed as being representative of the full extent and scope of the present invention. That is, these and other aspects and advantages will be apparent from the disclosure of the invention(s) described herein. Further, the above-described embodiments, aspects, objectives, and configurations are neither complete nor exhaustive. As will be appreciated, other embodiments of the invention are possible using, alone or in combination, one or more of the features set forth above or described below. Moreover, references made herein to "the present invention" or aspects thereof should be understood to mean certain embodiments of the present invention and should not necessarily be construed as limiting all embodiments to a particular description. The present invention is set forth in various levels of detail in the Summary of the Invention as well as in the attached drawings and the Detailed Description of the Invention and no limitation as to the scope of the present invention is intended by either the inclusion or non-inclusion of elements, components, etc. in this Summary of the Invention. Additional aspects of the present invention will become more readily apparent from the Detail Description, particularly when taken together with the drawings.

BRIEF DESCRIPTION OF THE DRAWINGS

The accompanying drawings, which are incorporated in and constitute a part of the specification, illustrate embodiments of the invention and together with the general description of the invention given above and the detailed description of the drawings given below, serve to explain the principles of these inventions.

Figure 1:
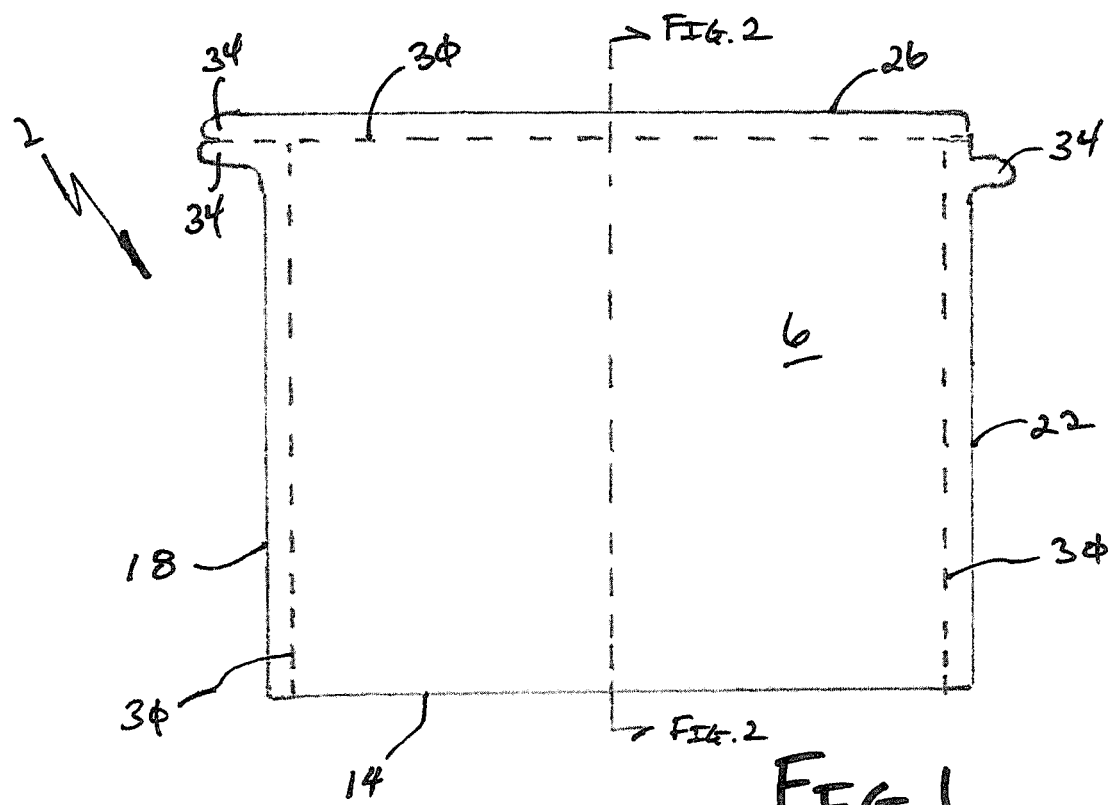
FIG. 1 is a front elevation view of a disinfecting wipe of one embodiment of the present invention.

The following component list and associated numbering found in the drawings is provided to assist in the understanding of one embodiment of the present invention:

Component
2 Disinfecting wipe
6 Outer layer
10 Inner layer
14 Fold line
18 Left lateral edge
22 Right lateral edge
26 Upper edge
30 Tear line
34 Tab
38 Fluid pocket
40 Handle
44 Grip
102 Disinfecting wipe
106 Outer layer
110 Inner layer
114 Fold line
118 Boundary edge
130 Tear line
134 Tab
302 Disinfecting wipe
318 Outer edge
350 Outer seal
354 Inner seal
360 Textured surface The drawings are not necessarily to scale. In certain instances, details which are not necessary for an understanding of the invention or which render other details difficult to perceive may have been omitted. It should be understood, of course, that the invention is not necessarily limited to the particular embodiments illustrated herein.

DETAILED DESCRIPTION

FIGS. 1-9 show disinfecting wipes contemplated by embodiments of the present invention. The wipes are constructed of an inner layer of fluid-permeable material bonded to an outer layer made of impermeable material. Before use, the outer layer is folded such that the inner layer is contained and contact therewith the is prevented. Tear lines, or other selective interconnection mechanisms, are provided on the outer layer that allow for selective removal of a portion thereof. After portions of the outer layer are removed, the disinfecting wipe is open to expose the inner layer. The user can, thus, avoid contact with the inner layer by only touching the outer layer.

Figure 2:
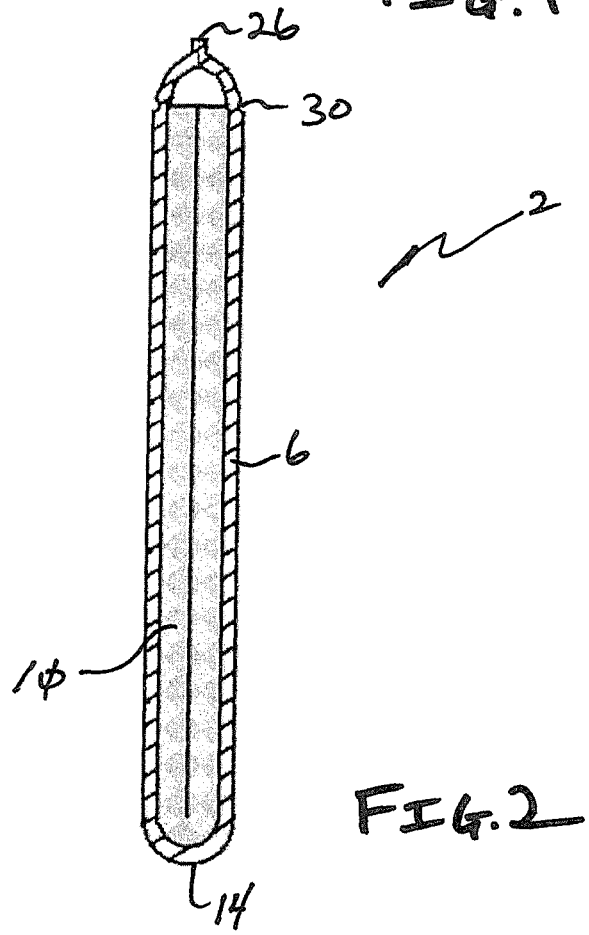
FIG. 2 is a cross-sectional view of FIG. 1.
Figure 3:
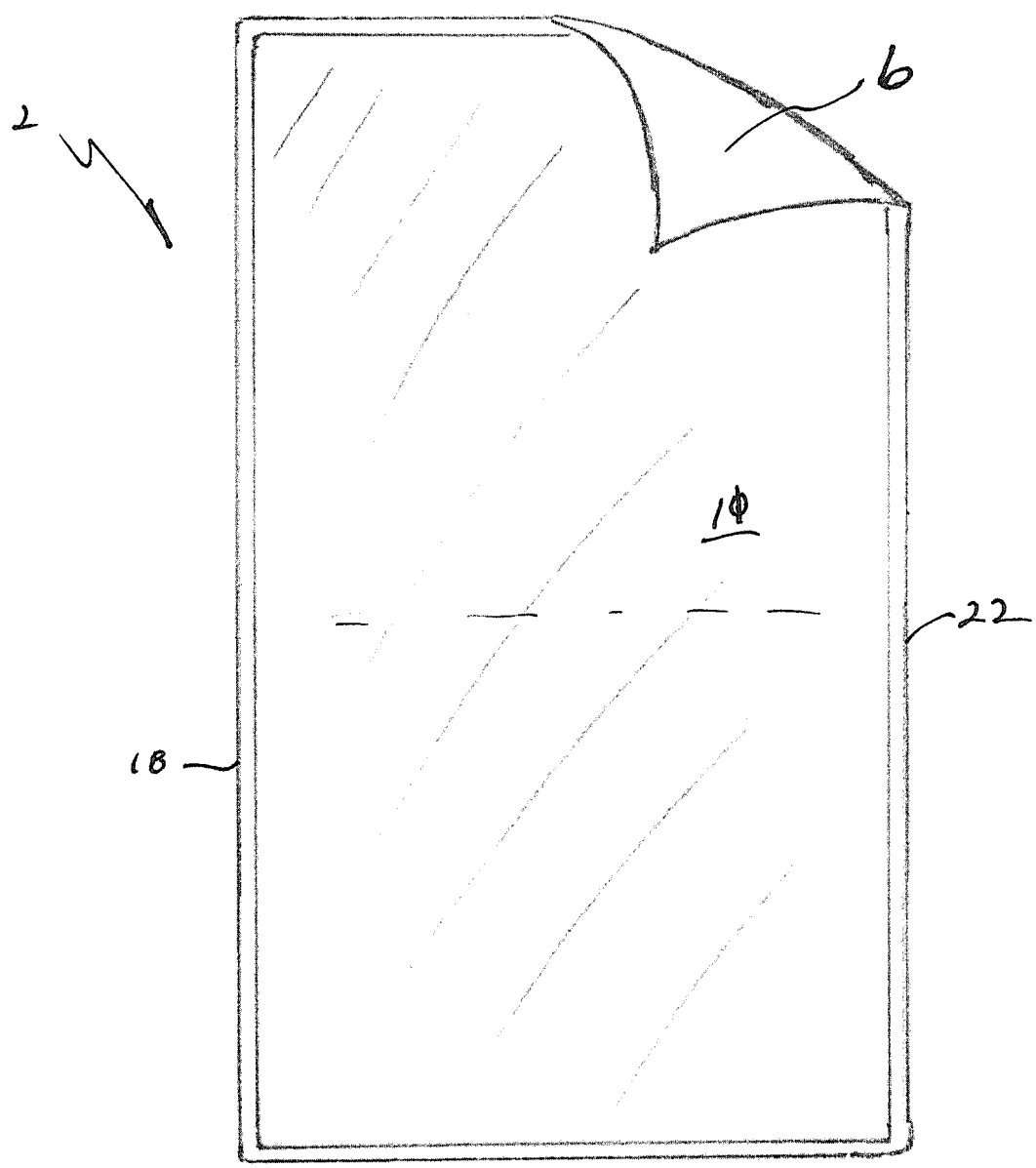
FIG. 3 is a front elevation view of the disinfecting wipe shown in FIG. 1 in a second position of use.

FIGS. 1-3 show the disinfecting wipe 2 of one embodiment of the present invention that has a generally square or rectangular profile with an outer layer 6 interconnected to an inner layer 10. The outer layer 6 is folded to create a fold line 14, a left lateral edge 18, a right lateral edge 22, and an upper edge 26. The left lateral edge, right lateral edge, and upper edge of our interconnected by selective interconnection mechanisms, such as ultrasonic welds, that are associated with tear lines 30. Tabs 34 associated with the upper edge, left lateral edge, and/or right lateral edge may also be provided to facilitate or to enhance user grip, which allows a portion of the outer surface to be removed easily. After the upper and lateral edges are removed from the outer layer, the outer layer is unfolded to reveal the inner layer comprised of an absorbent material.

Figure 4:
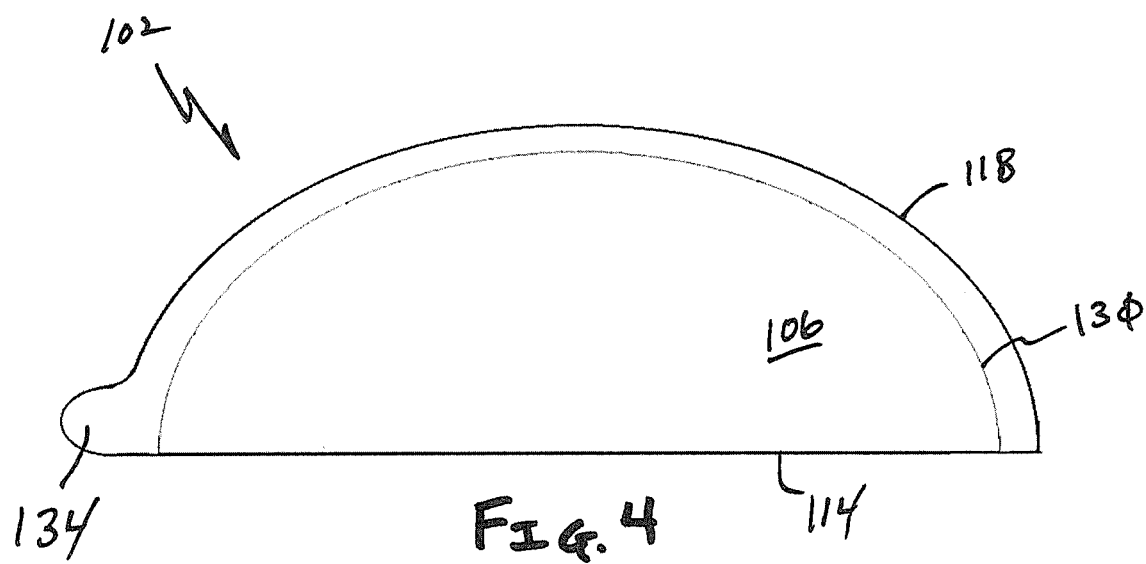
FIG. 4 is a front elevation view of the disinfecting wipe of another embodiment of the present invention.
Figure 5:
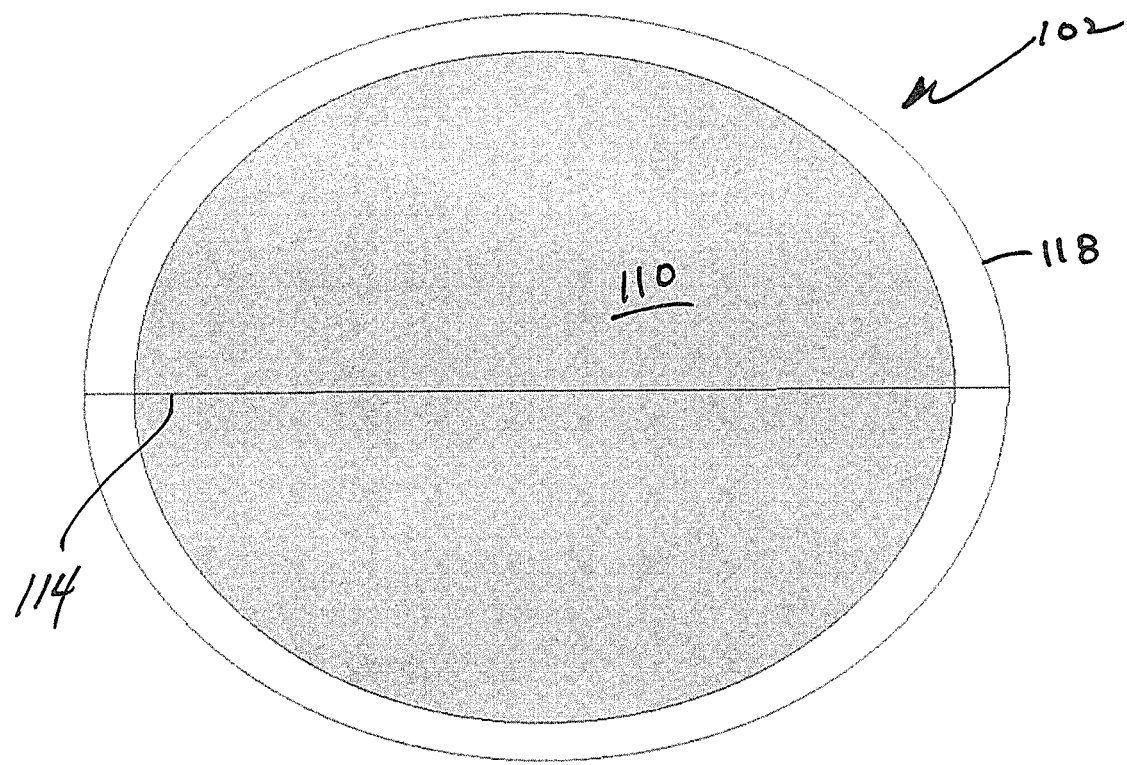
FIG. 5 is a front elevation view of the disinfecting wipe shown in FIG. 4 and a second position of use.

FIGS. 4 and 5 show another embodiment of the disinfecting wipe 102 that is generally circular or oval when open. As in the embodiments described with respect to FIGS. 1-3, this embodiment of the present invention has an outer layer 106 interconnected to an inner layer 110. A fold line 114 is created when the outer layer 106 is sealed and the disinfecting wipe assumes a generally semi-circular shape. An ultrasonic weld bonds a boundary edge 118 of the outer layer, thereby fluidic integrity within the folded outer layer 106 is maintained. A tear line 130 is created at a predetermined distance from the boundary edge 118, which also defines a removable portion of the outer layer. The boundary edge 118 is torn away from the outer layer 1062 permit opening of the outer layer so that the inner layer can be exposed.

Figure 6:
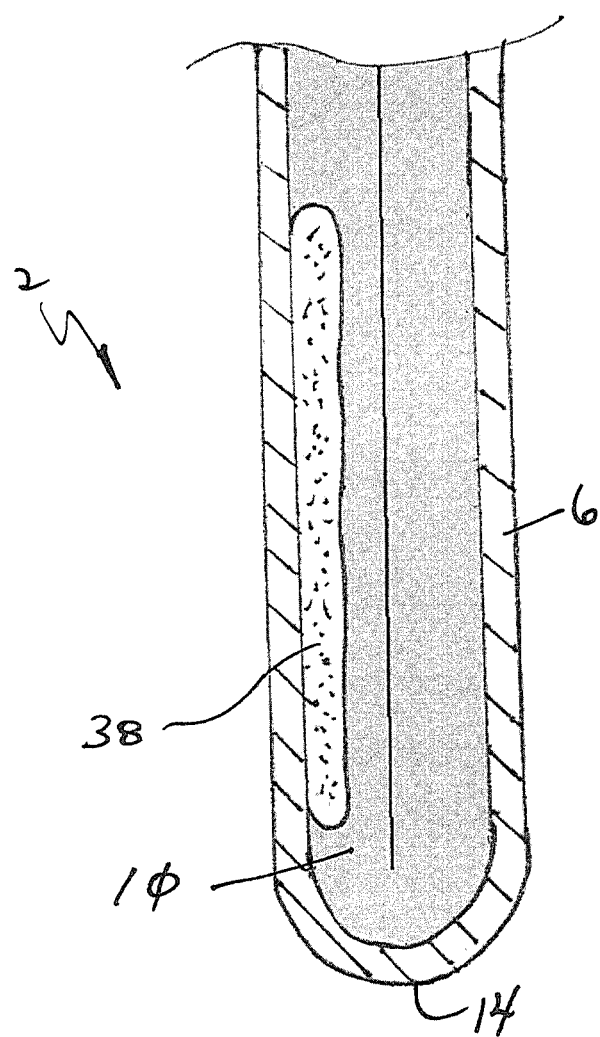
FIG. 6 is a cross-sectional view of a disinfecting wipe of another embodiment of the present invention.

FIG. 6 is a cross-sectional view of an alternate embodiment of the present invention that employs a fluid pocket 38. The pocket 38 separates the disinfecting or cleaning solution from the inner layer 10, which helps maintain the fluid's efficacy and the integrity of the inner layer. The pocket 38 also ensures the inner layer will be moist when needed. The pocket 38 is positioned within the thickness of the inner layer 10 or between the outer layer and the inner layer. The user selectively ruptures the pocket prior to or after opening, thereby allowing the contained fluid to permeate the inner layer. The pocket 38 is preferably ruptured by selectively pressing on or bending the outer layer 6 in the sealed configuration so that contact with the inner layer is avoided. The pocket may be positioned in such a way to span the fold line, wherein the act of unfolding will rupture the pocket and released a fluid therefrom. The fluid may be injected into the inner layer (or pocket) through an opening in the outer layer. To prevent fluid egress, any opening in the outer layer can be later sealed. One of ordinary skill in the art will appreciate that multiple pockets can be provided. In this example, each pocket does not necessarily contain the same fluid.

Figure 7:
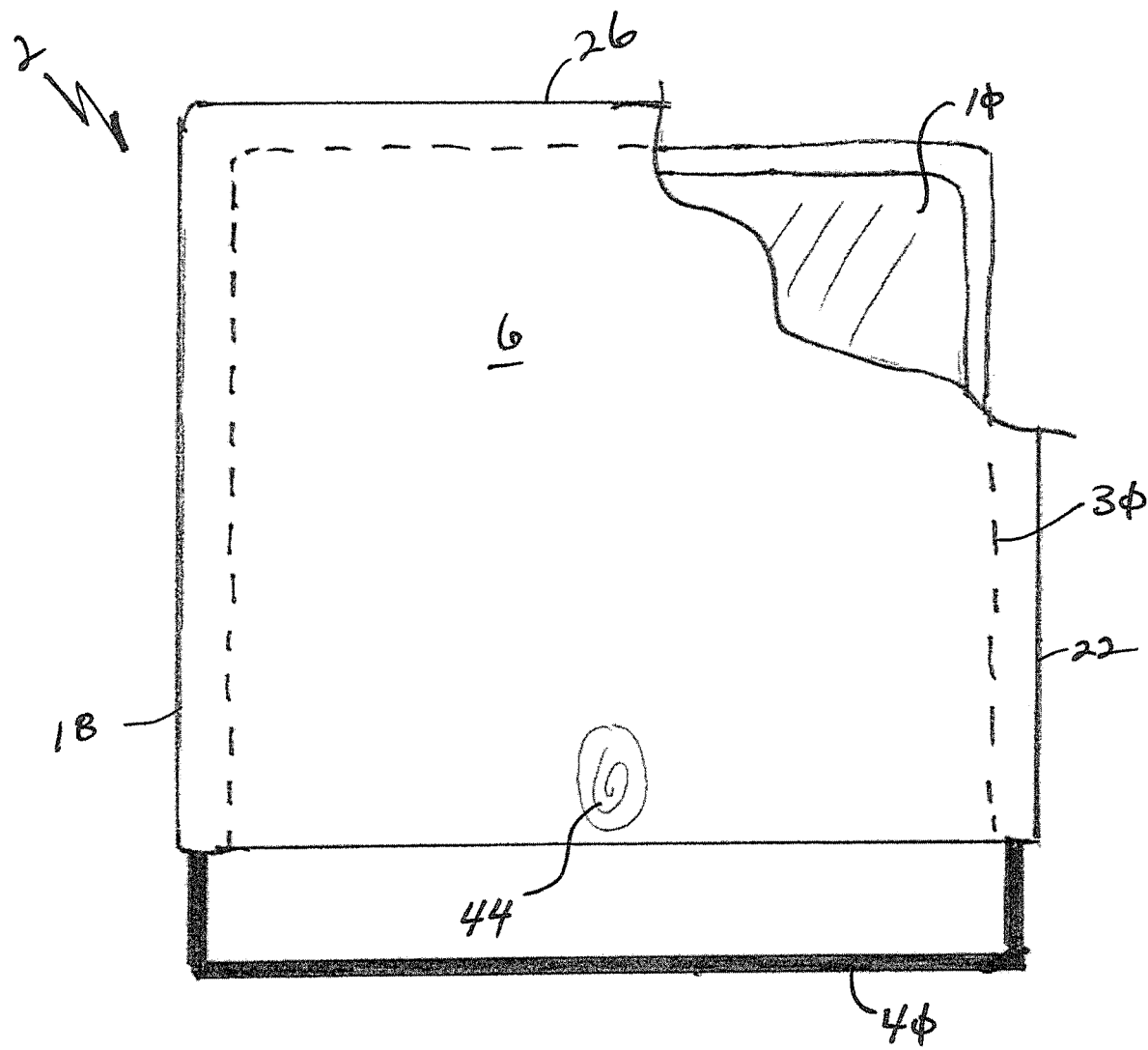
FIG. 7 is a front elevation view of a disinfecting wipe of another embodiment of the present invention that employs a handle.

FIG. 7 shows another embodiment of the present invention that employs a handle 40 instead of a tab to facilitate removal of portions of the outer layer 6 to expose the inner layer 10. Here, as in the embodiments provided above, a tear line 30 is provided in the sealed outer layer. The handle 40 is interconnected to edge portions designed to be removed from the outer layer. A grip 44 may be provided to help the user firmly grasped the fold line 14 while the user's other hand is used to grasp the handle 40 and tear the left lateral edge 10, right lateral edge, and upper edge 26 from the outer layer 6. This action allows the outer layer to be opened to expose the inner surface 10 and the remaining portions of the outer layer.

Figure 8:
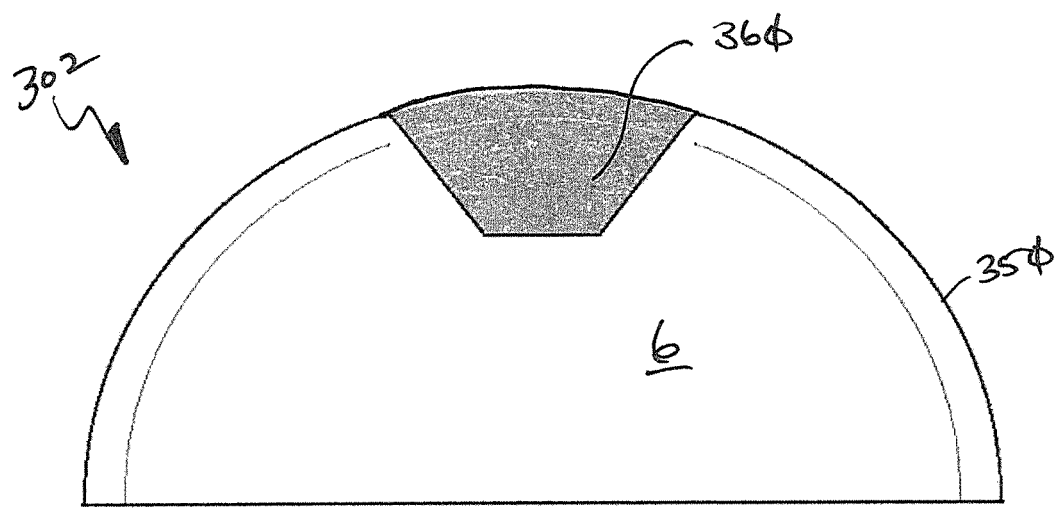
FIG. 8 is a front elevation view of a disinfecting wipe of another embodiment of the present invention shown in a closed configuration.
Figure 9:
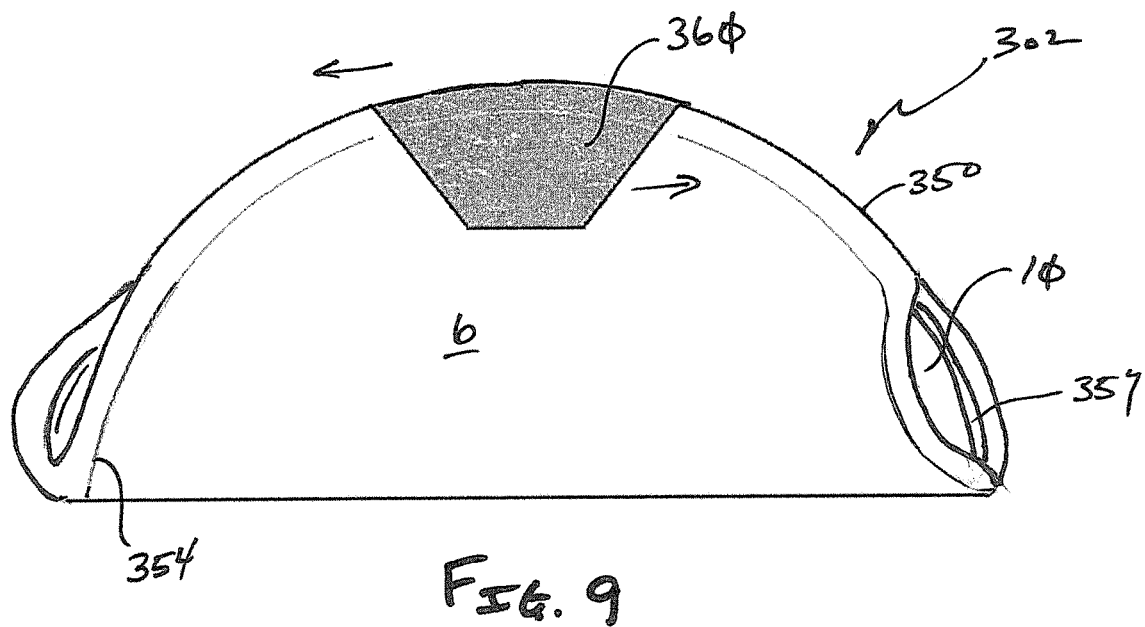
FIG. 9 is a front elevation view of the disinfecting wipe of FIG. 8 shown in a semi-opened state.

FIGS. 8 and 9 show a disinfecting wipe 302 of another embodiment of the present invention that employs a weak outer seal 350 and a selectively interconnectable inner seal 354. The inner seal may be a Ziploc® type seal and the outer seal may be a weak ultrasonic weld. This configuration helps ensure the inner seal 354 is difficult to access, which helps avoid unintended opening of the disinfecting wipes. A textured surface 360 may be provided along the outer edge 318 of the folded disinfecting wipe. The textured surface helps the user slide portions of the outer surface in opposite directions, which puckers the outer layer and, thus, breaks the outer seal 350 in at least one location. The break in the outer seal exposes the inner seal and allows the user to grasp the inner surface and outer surface of the outer layer which facilitates separation of the inner seal. Again, breaking of both seals allow the user to unfold the outer layer to expose inner layer. Those of ordinary skill in the art will appreciate that the inner seal may be a weak or strong ultrasonic weld. In addition, adhesives can be used alone or in conjunction with ultrasonic welds. And more than two seals may be provided. Depending on the nature of the seals employed, the outer layer may be resealable.

While various embodiments of the present invention have been described in detail, it is apparent that modifications and alterations of those embodiments will occur to those skilled in the art. It is to be expressly understood that such modifications and alterations are within the scope and spirit of the present invention, as set forth in the following claims. Further, it is to be understood that the invention(s) described herein is not limited in its application to the details of construction and the arrangement of components set forth in the preceding description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

What is claimed is:

1. A wipe, comprising:
a fluid impermeable first layer having an outer edge, the first layer capable of being configured into a first, closed position of use, wherein the outer edge is divided to define a first outer edge portion that is aligned with a second outer edge portion, and a second, open position of use, wherein the first outer edge portion and second outer edge portion are separated;
a second layer at least partially made of a fluid permeable material interconnected to an inner surface of the first layer, the second layer having an outer edge spaced from the outer edge of the first layer, wherein when the first layer is in the first, closed position of use, portions of the first layer adjacent to the outer edge thereof engage to form an overlap area that bounds the second layer;
a bond provided on the overlap area that forms a substantially air-tight seal that is adapted to be selectively severed to allow removal of portions of the first layer to expose the second layer; and
wherein the first layer includes at least one sheath adapted to receive a portion of a finger.

2. The wipe of claim 1, wherein the second layer is selectively removable from the first layer.

3. The wipe of claim 1, further comprising a selectively breakable pocket containing disinfecting solution positioned between the first layer and the second layer.

4. The wipe of claim 1, wherein a grip is provided on a portion of the first layer, the grip having a texture that differs from that of the remainder of the first layer.

5. The wipe of claim 1, wherein when the first layer is in the first, closed position of use, the second layer is not folded.

6. The wipe of claim 1, wherein the second layer is wetted with fluid that is a disinfecting solution, a cleaning solution, a wax, a polish, a polish remover, or a fluid that includes alcohol.

7. The wipe of claim 6, wherein the second layer is a first color when the fluid content thereof is at first level and a second color when the fluid content thereof is at a second level.

8. A wipe, comprising
a fluid impermeable first layer having an outer edge, the first layer capable of being configured into a first, closed position of use, wherein the outer edge is divided to define a first outer edge portion that is aligned with a second outer edge portion, and a second, open position of use, wherein the first outer edge portion and second outer edge portion are separated;
a second layer at least partially made of a fluid permeable material interconnected to an inner surface of the first layer, the second layer having an outer edge spaced from the outer edge of the first layer, wherein when the first layer is in the first, closed position of use, portions of the first layer adjacent to the outer edge thereof engage to form an overlap area that bounds the second layer;
a bond provided on the overlap area that forms a substantially air-tight seal that is adapted to be selectively severed to allow removal of portions of the first layer to expose the second layer; and
the wipe further comprising a selectively breakable pocket containing disinfecting solution positioned between the first layer and the second layer.

9. The wipe of claim 8, wherein the second layer is wetted with fluid that is a disinfecting solution, a cleaning solution, a wax, a polish, a polish remover, or an alcohol.

10. The wipe of claim 8, wherein the second layer is a first color when the fluid content thereof is at first level and a second color when the fluid content thereof is at a second level.

11. The wipe of claim 8, wherein the fluid is a disinfecting solution, and wherein the second layer is a first color when the disinfecting solution is of a first character and a second color when the disinfecting solution is of a second character, the first character and second character related to the age or effectiveness of the disinfecting solution.

12. The wipe of claim 8, wherein the overlap area includes perforated portions associated with the bond that facilitates removal of portions of the first layer so the wipe can be transitioned from the first, closed position of use to the second, open position of use.

13. The wipe of claim 8, wherein the bond is re-sealable.

14. The wipe of claim 8, wherein the second layer is selectively removable from the first layer.

15. The wipe of claim 8, wherein the first layer includes at least one sheath adapted to receive a portion of a finger.

16. A wipe, comprising:
- a fluid impermeable first layer having an outer edge, the first layer capable of being configured into a first, closed position of use, wherein the outer edge is divided to define a first outer edge portion that is aligned with a second outer edge portion, and a second, open position of use, wherein the first outer edge portion and second outer edge portion are separated,
- a second layer at least partially made of a fluid permeable material interconnected to an inner surface of the first layer, the second layer having an outer edge spaced from the outer edge of the first layer, wherein when the first layer is in the first, closed position of use, portions of the first layer adjacent to the outer edge thereof engage to form an overlap area that bounds the second layer;
- a bond provided on the overlap area that forms a substantially air-tight seal that is adapted to be selectively severed to allow removal of portions of the first layer to expose the second layer; and
- wherein a grip is provided on a portion of the first layer, the grip having a texture that differs from that of the remainder of the first layer.

17. The wipe of claim 16, wherein the fluid is a disinfecting solution, and wherein the second layer is a first color when the disinfecting solution is of a first character and a second color when the disinfecting solution is of a second character, the first character and second character related to the age or effectiveness of the disinfecting solution.

* * * * *